(12) United States Patent
Million

(10) Patent No.: US 11,146,867 B2
(45) Date of Patent: Oct. 12, 2021

(54) APPARATUS AND METHOD FOR OBTAINING AND PROCESSING DATA RELATING TO USER INTERACTIONS AND EMOTIONS RELATING TO AN EVENT, ITEM OR CONDITION

(71) Applicant: Blue Yonder Research Limited, Leeds (GB)

(72) Inventor: Jonathan Million, Leeds (GB)

(73) Assignee: Blue Yonder Research Limited, Leeds (GB)

(*) Notice: Subject to any disclaimer, the term of this patent is extended or adjusted under 35 U.S.C. 154(b) by 0 days.

(21) Appl. No.: 16/600,727

(22) Filed: Oct. 14, 2019

(65) Prior Publication Data
US 2020/0120403 A1    Apr. 16, 2020

(30) Foreign Application Priority Data

Oct. 12, 2018 (GB) .................................. 1816647
Dec. 11, 2018 (GB) .................................. 1820128

(51) Int. Cl.
*G06Q 30/02* (2012.01)
*H04Q 9/00* (2006.01)

(52) U.S. Cl.
CPC ........... *H04Q 9/00* (2013.01); *H04Q 2209/40* (2013.01); *H04Q 2209/82* (2013.01)

(58) Field of Classification Search
None
See application file for complete search history.

(56) References Cited

U.S. PATENT DOCUMENTS

| | | | | |
|---|---|---|---|---|
| 2008/0065468 A1* | 3/2008 | Berg | ...................... | G06Q 30/02 705/7.32 |
| 2008/0097769 A1* | 4/2008 | Galvin | .................... | G06Q 30/02 705/346 |
| 2015/0186959 A1* | 7/2015 | Koljonen | ........... | G06Q 30/0282 705/347 |
| 2017/0269759 A1* | 9/2017 | Marshall | ............. | G06F 3/03547 |
| 2019/0098445 A1* | 3/2019 | Hu | ......................... | H04W 4/33 |

* cited by examiner

*Primary Examiner* — Curtis A Kuntz
*Assistant Examiner* — Jerold B Murphy
(74) *Attorney, Agent, or Firm* — McKee, Voorhees & Sease, PLC

(57) ABSTRACT

The invention relates to a system, device, method and apparatus for providing the input of user response data into a device body and the transmission of the data from the device body to a further device for processing of the data and then typically for collecting the data for a number of persons to allow an overview to be generated of the individual and group of persons experience sand responses with regard to one or more parameters of a particular item, event or service that the persons have interacted with. The invention allows the data to be generated by the person at or close to the time that the experience or experiences occur and in a relatively user friendly manner and therefore allow a more accurate and reliable indication of the user interaction to be achieved, and hence more detailed and accurate feedback to be provided to the item, event or service provider.

24 Claims, 6 Drawing Sheets

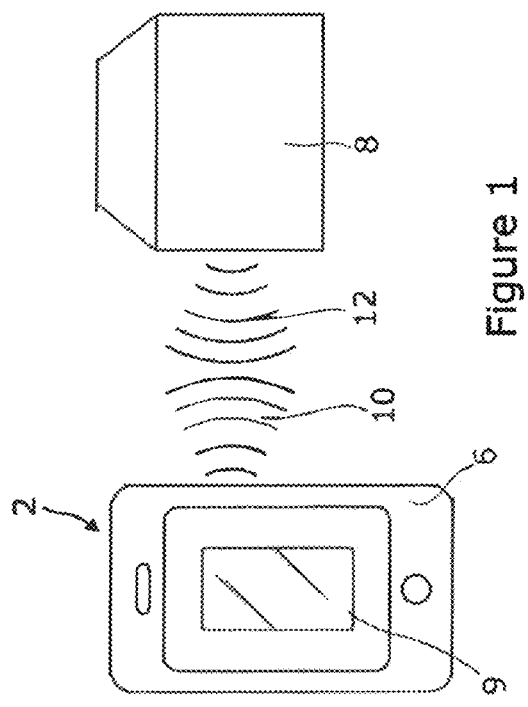
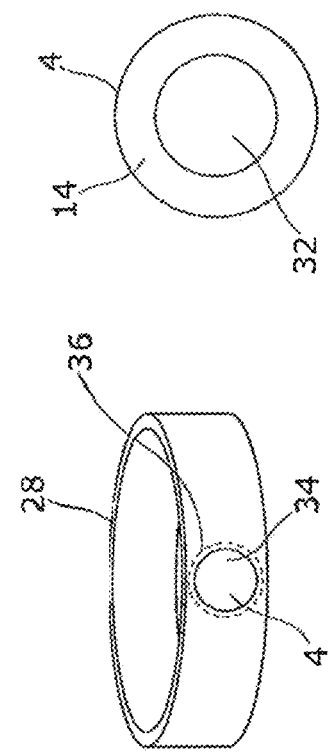
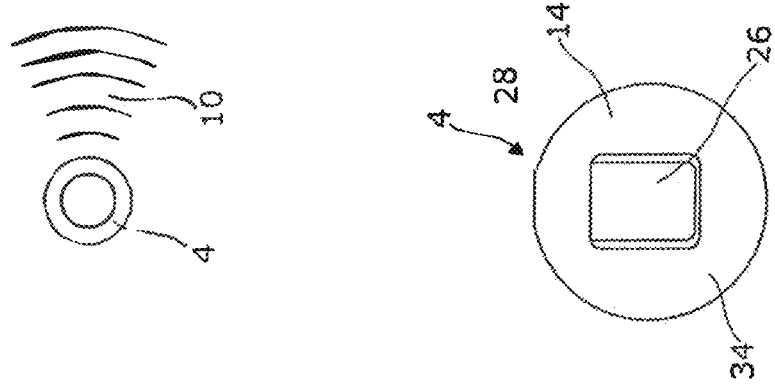

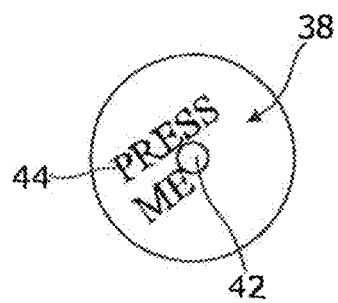 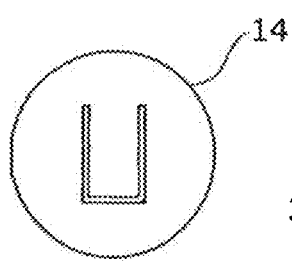 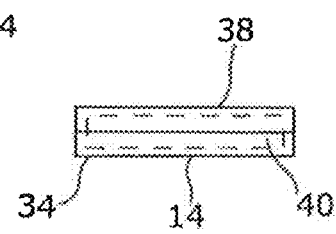
Figure 3a     Figure 3b     Figure 3c
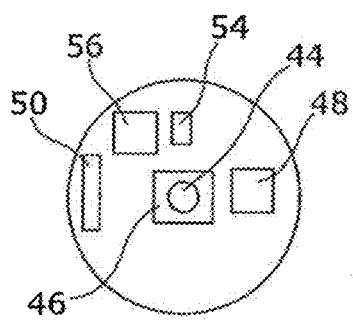 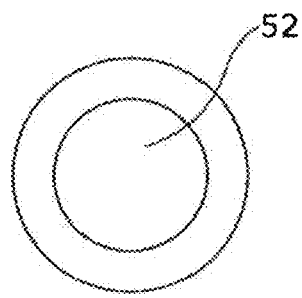
Figure 4a     Figure 4b
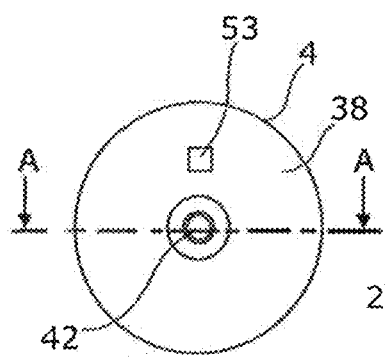 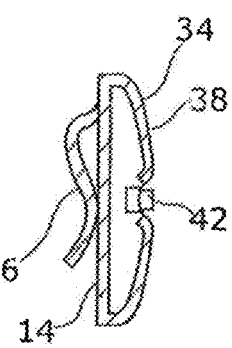 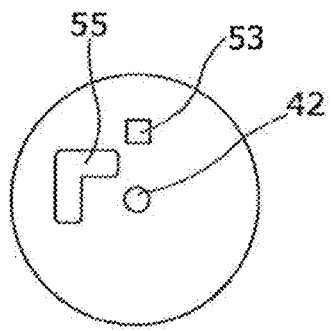
Figure 9a     Figure 9b     Figure 9c

APPARATUS AND METHOD FOR OBTAINING AND PROCESSING DATA RELATING TO USER INTERACTIONS AND EMOTIONS RELATING TO AN EVENT, ITEM OR CONDITION

CROSS-REFERENCE TO RELATED APPLICATIONS

This is a U.S. Application which claims priority to GB1816647.0, filed Oct. 12, 2018, and GB1820128.5, filed Dec. 11, 2018, all of which are herein incorporated by reference in their entireties.

FIELD OF INVENTION

The invention to which this application relates is apparatus and a method for collecting data relating to at least one parameter of an item, event or service. In particular, although not necessarily exclusively the parameter is in relation to a representation of a person's feedback and/or emotion relating to their interaction with the item, event or service.

BACKGROUND OF THE INVENTION

Examples of the item, service or event could be that the item may be a consumer item or article which the person has purchased or has been given and asked to use as a trial, the event may be a sporting occasion, musical occasion, an experience of participating in an organised social media or marketing occurrence, a person accessing an advert or series of adverts in a particular location or locations, a trial such as a clinical or medical trial within research, relating to new medication, heart monitoring, diabetes or the like and the service may be a public service, such as a transport, health, security service or a government service, a service provided by a private company such as an insurer, law firm, accountancy service or the like, or may be a method of allowing a person's health to be monitored by allowing the person to provide feedback representative of, for example, their mental health at a particular times, their compliance, or non-compliance with a treatment schedule such as, for example, giving up alcohol, cigarettes or the like.

In particular, although again not exclusively, the invention can be utilised in relation to the collection of data which is related to the frequency of usage of the item, event or service and/or satisfaction of the usage experience and the collected data from one person may be collated, along with data from other persons and processed in order to generate one or a plurality of indicators relating to the particular item, event or service.

The collection of data which is representative of consumer's preferences in relation to particular items and the use of the same, is known and relied upon by manufacturers of items and the providers of services in their decision making in relation to the future planning and provision of said items or events. For example, decisions can be made as to whether to continue to manufacture and sell the items, the consumers to which to direct marketing and promotions in relation to the said items and/or the manner in which certain services are provided and/or trials are managed. The reliance upon this information is such that the known problems of accuracy and ability to collect the data, are tolerated due to the importance of any data of this type.

One area of concern is the accuracy of indications of usage of an item as, while a representative subset of persons can be trained and paid to provide information relating to the usage of a particular item, service or take part in a trial it can still often be the case that the subset of consumers do not provide accurate feedback as to their usage of the item. The inaccuracy in the usage data may be due simply due to forgetfulness of the person who, while they may have every intention of providing feedback, may forget to do so, and/or the person may be under pressure in relation to time and/or other issues may arise to prevent the feedback and/or the feedback which is generated is sporadic inasmuch that while it may accurately indicate usage of the items at certain times, it does not provide accuracy of use at all times. Another problem is that there is human error in that the feedback which is provided is not that which was intended by the person.

As such, the data which is provided as feedback may have surprisingly low levels of accuracy.

In one form the data which is collected, is collected simultaneously, or substantially simultaneously with the user interaction with the item, service or event and so the data generated by the user is effectively live in that it reflects the user's feelings at that time of use of the item, service or event. This form of response is known as System 1 response.

This is in contrast to another form of data collection in which, at some time after, often a significant time after, the user accesses a means whereby they can log their feelings of the item, service or event. It is found in practice that the delay between the user interaction and the logging of their feeling, means that the user may not in fact log their feelings at all; may be influenced by another occurrence between the time of the user interaction and the time of logging their feeling which can skew the subsequent login and/or the time between the user interaction and the logging of their feeling allows the user time to think and consider their response which then means that the response is in effect, what is known as a System 2 response.

There is a great desire within many commercial activities to be able to retrieve the System 1 rather than System 2 data.

Previous attempts to provide systems and apparatus to allow feedback to be provided by the user have been found to be cumbersome and time consuming so that no significant advantage is obtained.

An aim of the present invention is to provide apparatus and a method which enables a consumer to provide feedback data in relation to certain parameters for an item, event or service and so allow the feedback to be provided more easily and accurately by the consumer and therefore allow the data which is received, to be regarded as having a greater reliability and accuracy. A further aim is to provide the ability for the efficient collection of system 1 data.

In a first aspect of the invention, there is provided apparatus for use by a person to provide feedback relating to at least one parameter in relation to a particular item, event or service with which the person interacts, wherein said apparatus includes a device body, at least one user interaction means located with or on the device body for selective use by the person and a transmitter, said data representative of the said user interaction to be stored in and/or transmitted from the device body to a database for collection and further processing.

In one embodiment the apparatus includes control means to allow a type of user interaction to be linked to the at least one particular parameter or an element thereof. In one embodiment the control means is provided as part of the device body.

In one embodiment the device body includes transmission means such that any data generated from the user interaction means is automatically transmitted to another device. In one embodiment the device body includes a memory which has sufficient capacity to allow the temporary storage of data from the user interaction means so as to allow the same to be stored until subsequently transmitted from the device body to another device when a wireless transmission system is available to be used.

In one embodiment the device body includes memory means which stores the data from the user interaction means until the device body is connected to another device to allow the transfer of data from the device body memory to another memory device.

In one embodiment, the apparatus allows data for two parameters in relation to the item, event or service to be generated by the user via the selected user interaction means.

In one embodiment, a first parameter is the usage of the item, event or service and the second parameter is the preference of the user with regard to their experience of use of the item, event or service and the user interaction means can be selectively operated in different ways to allow a particular parameter or element to be identifiable.

In one embodiment, the use of the item, event or service is generated as data linked to a particular time of the usage which can be identified by the user interaction means or as the time at which the data is transmitted from the device body or received at the said database.

In one embodiment, the selection of the data for the time of usage of the item, event or service is generated by the occurrence of the person operating the user interaction means and the generation of the data for the satisfaction of usage is achieved by the person operating the user interaction means in one of a number of possible configurations, such as one press to indicate a good satisfaction, two presses to indicate poor satisfaction within a given period of time.

In one embodiment, the transmission of the data from the user interaction means is via a wireless communication system from a transmitter on the apparatus to a further item of apparatus.

In one embodiment, the transmission is via a relatively low energy wireless system such as a Bluetooth (RTM) communication system and the data can be transmitted to a receiver such as the person's cellular phone, laptop or other communication means which is capable of receiving, and is in range of, the Bluetooth signal.

In one embodiment, the data which is transferred to the said receiver is then transmitted onwards to a remote location for further processing or is stored in a memory in said receiver apparatus memory for subsequent transmission and/or collection.

Typically, the further processing at the remote location, will include the processing of data from a plurality of persons using the apparatus and respective user interaction means as herein described.

In one embodiment, the device body is provided with retention means to allow the same to be carried on and by the said person such as on an item of clothing, jewelry, accessory or the like and/or to be located on an item which the person is to use and for which the data generated by the person using the user interaction means relates.

In one embodiment, the retention means are a clip or stud so as to allow the device body to be carried on an item of clothing of the user or to be attachable and carried as part of an article which is to be worn by the user such as, for example, a bracelet or band to be worn on the wrist.

In one embodiment, the retention means are, or include, an adhesive patch or sticker to allow the device body to be adhered to the item and therefore be available for user interaction at the time of use of the item.

Typically, the apparatus is provided with a power supply which allows the operation of the user interaction means and data transmitter.

In one embodiment, the power supply is a power cell located within the device body which, in one embodiment, can be provided so as to allow the apparatus to operate for a predetermined period of time.

In one embodiment, the apparatus is provided with control means to allow the apparatus to be activated at a particular time and deactivated at a particular time so as to define a period of time of available use.

In one embodiment, the control means allow a number of the user interaction means to be rendered operable and inoperable at the same time.

Thus, in accordance with the invention, there is provided a means of enabling user interaction to generate data relating to one or more parameters in relation to a particular identified item, event or service in an efficient manner and thereby allow the data generated to be transmitted for subsequent processing. By providing the item with the user interaction means located on a device body which can be worn, or attached to an item, then the accessibility of the said apparatus is improved and, in turn, this means that it is more likely that users will actually interact with the apparatus on a day-to-day basis and provide a more accurate representation of the said usage and preferences than is conventionally obtained.

In one embodiment the device body includes visual and/or audible indication means to indicate to the user the particular type of interaction that they have performed, whether the interaction is valid and/or that the device body is being reset and a previous interaction has been cancelled.

In embodiment the visual means is one or more LED's and the colour and/or condition of the LED's can be used to indicate different states of operation of the device body as well as the user interaction with the same.

In a further aspect of the invention, there is provided a device body for use by a person to provide feedback data relating to at least one parameter in relation to a particular item, event or service with which the person interacts, said device body including a housing, at least one user interaction button or surface located with or on the housing and available for selective use by the person and a memory located in the housing along with a power supply to allow data representative of the use of said at least one user interaction button or surface to be stored in and/or transmitted from the device body and wherein the said at least one user interaction surface is selectively operable in one or more configurations.

In one embodiment as the user interaction means can be operated in a number of different configurations then each of the configurations is linked to a particular parameter and/or parameter preference and the person is made aware of the same so that they can select which configuration to select.

In one embodiment audible and/or visual indication means are provided and the operation of which is linked to the state of operation of the device body.

In one embodiment the user interaction means include one/or more portions which can be activated by the user by touch or without contact to allow data representative of the user interaction configuration to be generated.

In accordance with a further aspect of the invention, there is provided a method of generating and collecting data from a person which is representative of their response to an item, event or service, said method comprising the steps of, identifying the item, event or service in relation to which the data is to be generated, providing a device body with user interaction means with which a user can interact to indicate usage or a time of experience of the item, event or service and/or an emotion in relation to the said item, event or service, and wherein the person is instructed to operate the user interaction means to generate data representative of said usage, experience and/or emotion at or close to the same time as the usage or experience occurred and transmitting and/or storing the data to allow the same to be further processed.

In one embodiment, the method includes the step of collating the data received from a number of persons using the said apparatus and processing the said collated data to generate indicators of the one or more parameter relating to a group of persons.

In one embodiment, the method includes the steps of identifying the said item and specifying a particular time period during which the said data is to be generated.

In one embodiment, the method includes the steps of rendering the said user interaction means as disposable by providing a power supply in the form of a power cell located in the device body which has a predetermined lifespan.

In one embodiment, the method includes the step of identifying a group of persons to whom the said apparatus is provided and instructed to provide user interaction so as to provide a particular defined group response.

In one embodiment the said item is a retail package such as toiletries, drinks, foodstuffs or the like.

In one embodiment the event is a service which is provided to the person such as a transport service, customer service and/or information service.

In one embodiment the event is a trial such as a medical or clinical trial or trial of another sort in which the person is participating.

In a further aspect of the invention there is provided a system including a user interaction device, a means for receiving data generated from the device and a data processing means and wherein the system allows System 1 data to be retrieved and subsequently processed.

Typically the user interacts with the device and thereby logs their response in relation to the interaction which they have recently had, or are having, with the particular item, event or service with which the device is linked.

In one embodiment, the current invention allows the data which is generated from the user interaction device to be allocated to and/or used in conjunction with other data sources such as, for example, biometric data for the particular user.

In one embodiment, the app which is provided includes means to collect biometric data relating to that user such as, for example, the number of steps, heartrate and other features and the said biometric data can be collected by the host of the app.

In one embodiment, the use of the biometric data allows an indication to be generated as to the activity of the user at the time of the user interaction device data being logged and this can be used to provide further information in relation to the particular use of a particular item, event or service.

In one embodiment any type of further data can be utilised in conjunction with the data from the user interaction device if it is believed that the further data would allow advantage and further insight into the analysis of the use of the item, event or service. In one embodiment this may be provided via smartphone and include any suitable further data that the smart phone may be able to collect now or in the future, such as, for example, eye movement or other activities being performed by the user at the time of interaction with their user interaction device and/or other occurrences at that time, such as particular adverts, music, other persons or noise in the environment during the use of the user interaction device.

Typically, the data received from the user interaction device, includes data representative of one or more operations of the device in a predetermined time period and data indicative of the time at which the user interaction with the device occurred.

In one embodiment, the data processing means at the app or at the database, includes one or more algorithms to determine the validity of the received data such as, for example, if the device has been used in a manner such as to cause repeated operations, as may be caused by a young child, then this can be detected and the validity of that group of data, may be questioned or disregarded.

In one embodiment, the data from the user interaction device is used in conjunction with data which is indicative of the location of the user interaction device. Again, in one embodiment, the GPS data can be obtained from the host on which the app is provided and with which the user interaction device is wirelessly connected. In another embodiment the device body and/or the further device with the which the device body communicates are provided with means to count the number of steps which the person wearing the device body and/or further device takes whilst being tasked to provided user response data via the device body.

The present invention thereby allows the recruitments of users who can be identified as being particularly relevant to the item, service and/or event or to whom the item service or event is relevant to and the users can be trained on how to use the system and, in one embodiment, can be encouraged to provided interaction, such as via daily activity reports, to encourage engagement between the user and the system provider. Furthermore, the system can be shown to motivate and engage users and thereby increase return response rates. The data which is retrieved and processed, can be broadcast live to the party which wishes to use the data, such as the provider of the service or event or the manufacturer of the item, via a dashboard and create any crosstabs that they may want to fulfil their own requirements.

In one embodiment, the device may include a microphone to accept comments from the user which can be used in combination with the data interaction which they have made via the device or may be used independently to provide further comments on the particular item, service or event which they are using.

In one embodiment, the app can also register the other activities of the user at the time of their interaction with the device such as, for example, is the user viewing the television and potentially viewing an advert in relation to the item, service or event.

In one embodiment, a report may be generated to indicate to the user whether there is any difference in their behaviour when interacting with the device versus their normal behaviour and may allow the user to interact either by scrolling through emoticons on their host such as a mobile phone or via a series of buttons which may be provided on the device.

It is also possible that further interaction means may be provided on the device so as to allow other selective interaction between the user and the system. For example, there may be provided more buttons on the user interaction device and/or more possible clicking sequences, in order to allow more choices for user interaction and hence feedback, such as to provide an increased range of possible user satisfaction ratings with regard to the particular item, event or service.

The invention therefore allows a wide range of possibilities including any or any combination of providing data which is representative of a user's experience of using, for example, a consumer item, so as to provide a feedback of whether or not they like the item, are satisfied with the performance or the like, could be representative of their experience of using a particular service such as a health service, transport service or the like, could be representative of the users awareness of one or more events such as for example, their awareness of when they see a particular advertisement, could be representative of the condition of the user such as for example, their mental well being over a period of time or could be used to provide support and back up to a user such as for example providing support in their attempts to stop taking a particular substance.

DESCRIPTION OF THE DRAWINGS

Specific embodiments of the invention are now described with reference to the accompanying Figures; wherein FIG. 1 illustrates in a schematic manner the apparatus in accordance with one embodiment of the invention;

FIGS. 2a-c illustrate a device body with retention means embodiments in accordance with the invention;

FIGS. 3a-c illustrate one embodiment of the device body exterior in accordance with one embodiment of the invention;

FIGS. 4a and b illustrate one embodiment of the device body interior in accordance with one embodiment of the invention;

FIGS. 9a-c illustrate a further embodiment of a device body in accordance with the invention.

Figure 5:
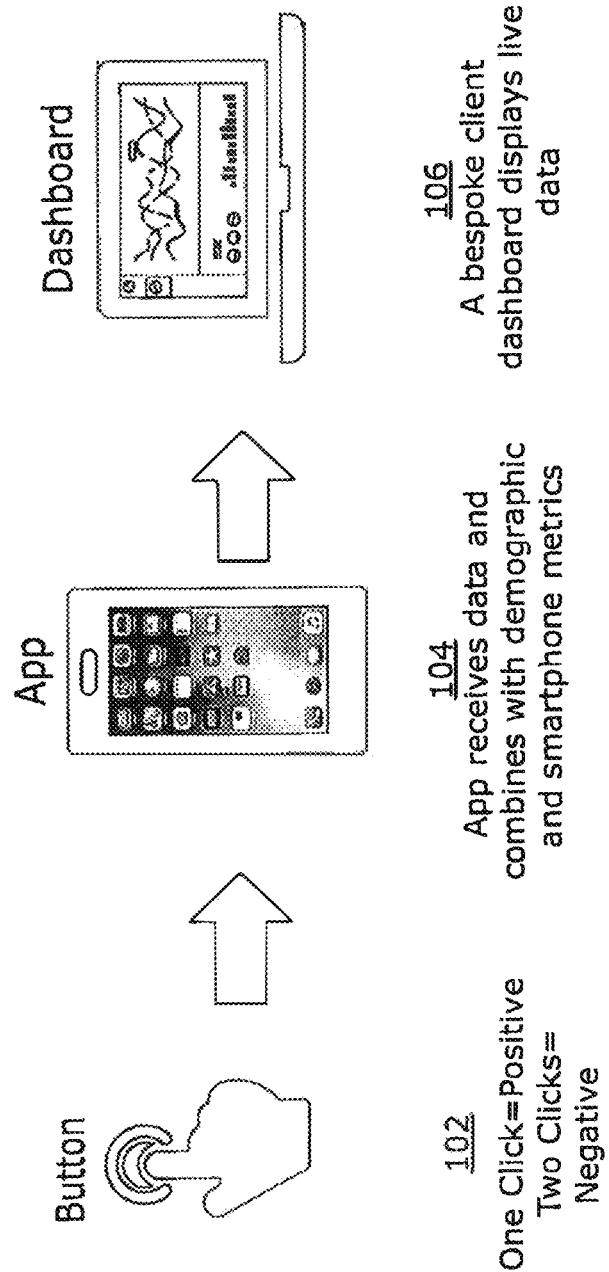
FIG. 5, illustrates schematically the system in accordance with one embodiment of the invention.

Referring firstly to FIG. 1 there is illustrated in a schematic manner, apparatus 2 in accordance with one embodiment of the invention. The apparatus includes a device body 4, a receiver 6 and a remote database 8. The device body is provided to be operable by a person in a manner which will be described subsequently to generate data. The data is then stored temporarily and/or transmitted 10 via transmission means located in the device body, such as a low energy Bluetooth transmitter, to the receiver 6 which, in this embodiment, is provided as the person's mobile telephone device. The device 6 may be provided with an application 9 with which the person can interact in relation to the data which is received from the device body 4 and/or via which the person can elect to transmit 10 the data from the receiver 6 to the remote database 8 such as by email, text message or the like or other data transmission means. At the remote database 8 the received data is collated and typically will be added to data from other persons, with the data relating to the same item, event or service with which the persons have all interacted. The grouped data can then be processed and used to provide information relating to the parameters of the item, event or service and then used as desired by the item, event or service provider. The remote database may also be able to transmit and communicate 12 with the receiver 6 and/or device body 4 so as to update or adapt the same.

It should be appreciated that although the system described in this example allows the transmission of data from the device body to a further device remotely, another embodiment of operation is for the data which is generated by the user interaction means of the device body to be stored in memory and then subsequently retrieved from the memory of the device body by a cable connection or the connection of another device thereto.

The device body 4 is provided with retention means to allow the same to be carried and/or attached when in use and three embodiments are illustrated in FIGS. 2a-c and a further embodiment is illustrated in FIGS. 9a-b. In FIGS. 2a and 9b, which is a sectional election of the device body housing along line AA, with the internal components removed, the rear face 14 of the device body 4 is shown and includes a clip portion 26 which is attached at the edge 28 to the housing 34 of the device body, with the remainder of the clip 26 being capable of being resiliently pivoted so as to allow a portion of, for example, an item of clothing to be trapped in the gap between the underside of the clip portion 26 and the rear face 14 and hence allow the device body 4 to be located on the clothing worn by the person.

In FIG. 2b the device body 4 is shown as having been located with a bracelet or band 28 which is provided to be worn on the wrist of the person, and in one embodiment this can be achieved by pushing the housing 34 into a cavity in the band with resilient side walls 36 around the cavity then retaining the device body 4 in position.

In FIG. 2c the rear face 14 of the device body 4 is provided with an adhesive patch 32 which has a masking layer which, when removed, exposes the adhesive and allows the device body 4 to be applied to and retained on the item in relation to which the device body is to be used.

The device body 4 can be provided in any shape and although shown as being circular is not limited to such as shape. The device body is shown in more detail with respect to FIGS. 3a,b,c and 4a,b and 9a-b.

The device body includes a housing 34 which has a front face 38 and a rear face 14 and defines a cavity 40 therein. In FIG. 3b the previously described rear face with a clip portion 26 is shown. In FIG. 3a the front face 38 is shown as having a user interaction means 42 located thereon which, in this embodiment is a button which can be depressed by pushing the same inwardly but in other embodiments may include a plurality of buttons for selective user interaction. As shown user instructions 44 can also be provided on the front face.

The button 42 is connected to an electronic switch device 46 in the cavity as shown in FIG. 4a and in FIG. 9c which shows a PCB in one form which may be housed in the device body, so that the depression of the button by the user is detected and the electronic switch device is connected to a data processor 48 which generates data signals which can be transmitted 10 from the device body 4 by transmitter components 50, or transceiver 55 and with reference to a clock 56 provided in the cavity. Also provided in the cavity is a power cell 52 which is connected to provide power for the operation of the device body for a period of time.

Visual and/or audible means may be provided as part of the device body and in one embodiment these are provided as light sources 53 as shown in FIG. 9c such as one or more LED's which provides a function to indicate to the person the type of their use of the user interaction means. For example, on each user interaction, typically for each "click" of the button 42 the control means will update whether one click or two or more clicks are received within a given time period. If one click is made correctly then the person will receive a visual indication of this by, for example the LED blinking in a particular colour for a period of time. If a double click is made the control means will update the total number of double clicks received and a visual indication that this has been logged will be generated by for example the LED operating in a different colour for a period of time. However if the person makes an error and wants to cancel the previous interaction they have a period of time to delete the previous interaction by, for example, depressing the button for a longer period, until the LED operates in another manner, for example in a further colour and which indicates to the person that the previous submission has been deleted. Thus it will be appreciated that the possibility of user interaction errors can be corrected in this manner and so the data which is generated can be ensured to have greater accuracy.

Typically the housing 34 is formed of a plastics material so as not to affect the wireless communication signals and the device body may have a diameter in the range of 30-40 mm and a thickness of 8-10 mm so that the same can be easily and comfortably worn by the person or attached to the item.

An example of the use of the invention is now provided.

In use there is therefore provided a wearable data logger capable of saving to a non-volatile memory in the device body, the data and the time, each time the button 42 is pressed. In the proximity of the data logger the person may have a smart phone device such as an android or iPhone phone running an app and so the device body and the app communicate with each other using Bluetooth BLE. Each time the button is pressed (single click or double click) the device body control means will advertise this to the app and the app will notify this to an online server. Once the data has been written in the server the app will indicate to the device body to delete the last entry and in this way maximise the available memory in the device body. Typically a software handshake mechanism is provided that doesn't allow loss of data. If the device body is not near the phone or tablet, it will store the data in a non-volatile memory 54 in the device body and will pass this information to the app whenever communication is subsequently possible.

In order to avoid accidental pressing, the button 42 may be provided with have a tactile effect to indicate that the button has been pressed and which requires a degree of force to be applied.

When the device body is first produced then, to save battery life, it will be in a "deep sleep" mode and in this mode the device body will only use a minimum amount of power. When a user receives a new device body they need to pair the device body with its app which can be done by pressing the button on the device body for a few seconds in order to advertise availability and then wait for an APP to pair.

Assuming a successful pairing, the person uses the app to update the internal time and user name. Once this has been done the device body will monitor the front button for click and double clicks.

On each click the control means will update the total number of clicks. On each double click (a double click is when a user presses the button twice in one second, the control means will update the total number of double clicks. Assuming the App is paired with the device body, the same will check the total number of clicks and when this number is non-zero, the app will read the time of clicks and the user id. The app will then try to send this information to the remote database 8 and if the data has been successfully written in the cloud then the app will ask the badge to delete the previous data.

Referring now to FIG. 5, there is illustrated the three elements of the invention in accordance with one embodiment and the three elements include a user interaction device 102 which has, in this embodiment, a button, which can be pressed by the user to record an interaction and, depending on the particular sequence of presses, to provide a feeling indication in relation to the interaction of the user with an item, service or event with which the system is linked at that time. For example, one click of the button within a predetermined period of time represents a positive feedback and two clicks of the button in the predetermined period of time indicates a negative feedback. The data which is generated is then transmitted wirelessly to a host device 104 such as a mobile phone which includes a control app and the data is typically transmitted along with a "timestamp" which indicates the time at which the data has been generated. The app can then onwardly transmit the data generated from the device 102 and/or transmits the data in combination with further data which may relate to the user demographic and/or smartphone metrics. Thus, the use of the host device 104 may be altered to suit particular uses of the system. The data is then transmitted from the host device 104 to a remote database 106 which receives data from a number of user devices and respective apps.

The device itself can be a relatively compact device which is Bluetooth enabled to allow the wireless transmission, has a relatively low energy usage to thereby extend the life of the battery held within the same, and may include branding on the same to more clearly link the device to a particular item, service or event with which the user is required to interact and provide their feedback.

The device 102 may also include a validation system, which may be indicated by light sources such as LEDs, to ensure that the device is logged to a particular system usage. The device may also include a memory located in the same, to log particular demographics relating to the user at that time and/or to store data which is generated but which cannot be communicated to the host device at that time and, when communication is restored, the data held in the memory can then be communicated to the host device and the app so as to ensure that all data which is generated is used.

Figure 6:
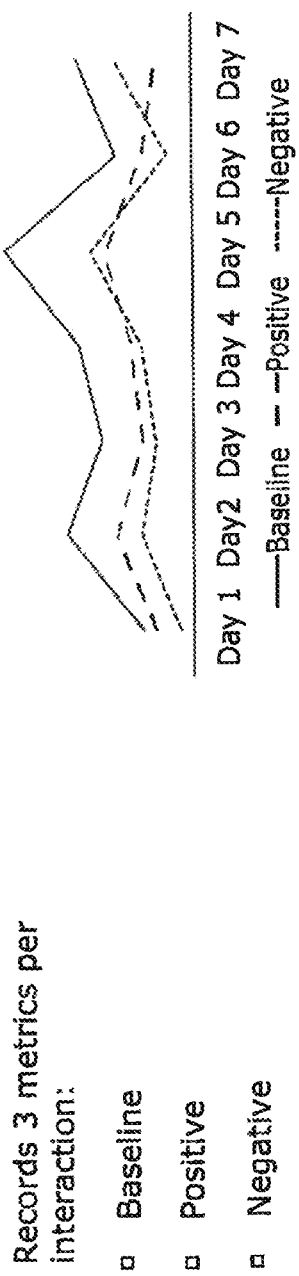
FIG. 6, illustrates graphically, the use of the data obtained from the device in accordance with one embodiment of the invention.

FIG. 6 illustrates graphically, the manner in which the data which is generated from the device 102 can be used to provide an indication of the baseline for the data and a breakdown of positive and negative responses over the given time period.

The host device and app for use of the same, can in one embodiment be initially connected and then remain connected thereafter so as to provide a user friendly interface and thereby further improve the likelihood that the user will provide the required interaction.

There may be an opportunity to allow the data which is received from the device 102, to be enriched by incorporating the same with further data and there may be a prompt facility provided to allow the host device 104 to generate prompts to the user if it is believed that the device is not being used. An internal messaging service may also be provided and a request for data from the device 102 may be made every predetermined period such as, for example, 0.5 seconds. Thus, the app and the host device 104 can be used to generate "in the moment" spontaneous insight into the user interaction with a specified item, event or service. In one embodiment, the host device instantly uploads the data which has been received to the remote data processing facility.

The app and host 104 may also interact with other apps which generate data on the host device or with other applications on other apparatus such as, for example, to obtain smartphone metrics including any or any combination of GPS, temperature, step counts, altitude, heartrate and/or activity levels.

Figure 7:
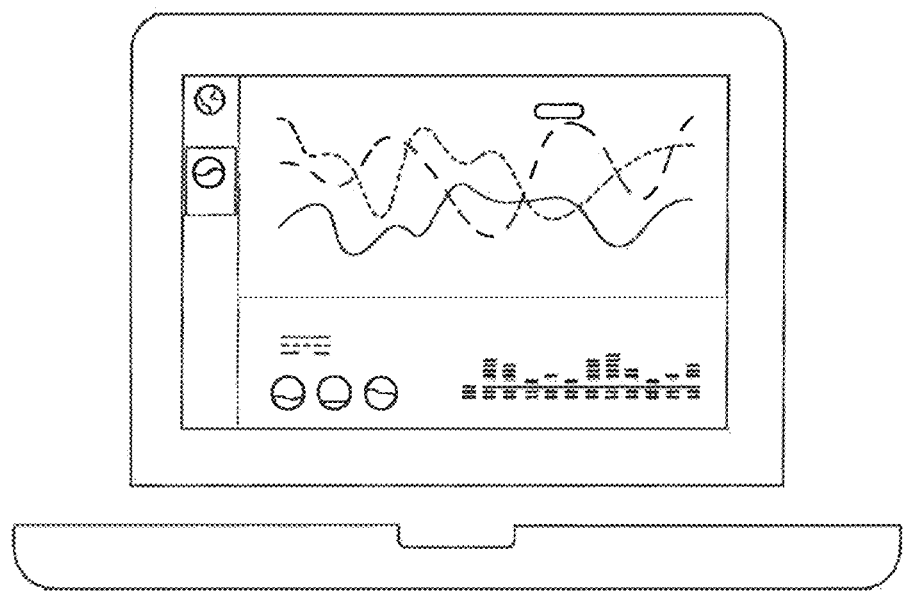
FIG. 7, illustrates the manner in which a database dashboard can be created.

At the data processing facility 106, a plurality of sets of data can be retrieved and then selectively processed together, in subsets or independently to generate a dashboard which provides, in one embodiment, a live data representation which may be updated every predetermined period of time such as one second. Furthermore, the dashboard can be created and utilised in a manner which is bespoke to a particular client's requirements. The data dashboard can also be accessed directly by the client i.e. the provider of the service, event and/or item so as to allow them to obtain a live indicator of the performance of the same. One example of the dashboard is provided in FIG. 7.

Figure 8:
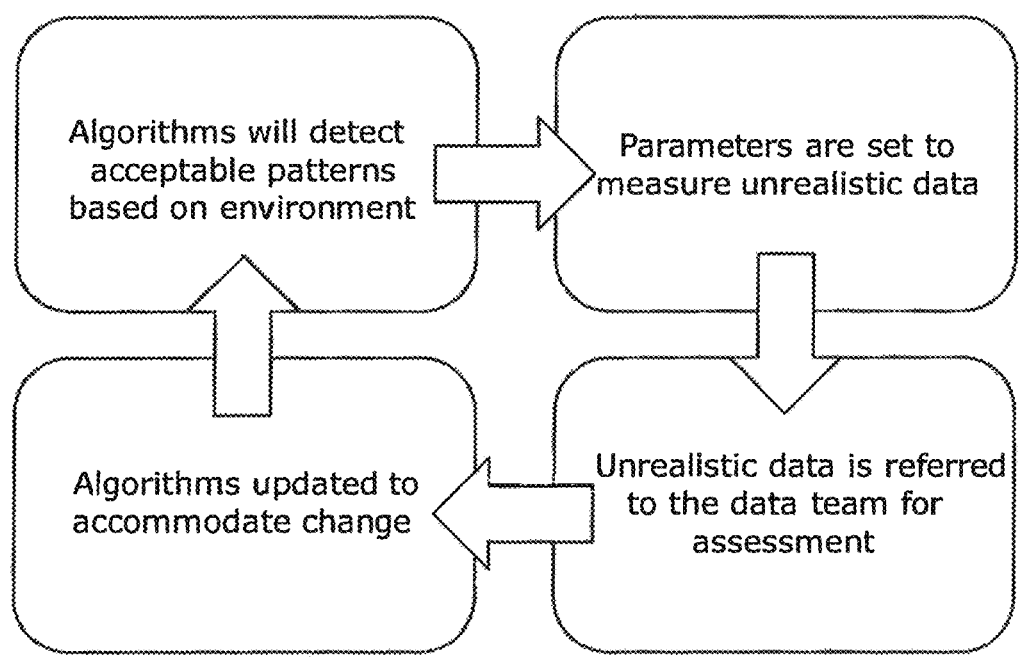
FIG. 8, illustrates the manner in which data checks may be provided on the data which is generated

FIG. 8 illustrates that the data processing apparatus can also include one or more algorithms to detect invalid data which has been received, such as that which has been created by a child playing with the button or the device, and then remove the unpredictable or potentially invalid data from the data processing and before the same is obtainable by the end user, and this is illustrated in FIG. 8.

It should be appreciated that further user interaction means can be provided on the device body so as to allow other selective interaction between the user and the system. In one embodiment this may be providing additional buttons or user interaction surfaces on the device, enabling more possible sequences of operation and/or providing additional functions such as apps which are provided on the further device such as the mobile phone with which the device connects.

The invention also includes the feature that the device can include a means for detecting a number of steps which a person performs while carrying the device body so as to allow the particular use of the user interaction means to be detected with regard to the persons activities at the same time. In addition or alternatively, there may be provided a GPS system so as to allow the particular location of the device body to be detected at any present time and, in particular, at the time of use of the user interaction means so as to allow the particular location of a person with regard to a particular item, event or service to be detected.

The item, service or event can be any activity such for example the use of a particular commercial item, the access of a particular service such as a health service, transport service or the like or attendance at a particular event such as a concert, promotional event, sporting event, product promotion or trial or the like. In particular environments, such as airports, the use of the device may be possible only within a particular defined area and in this case, using a local area network formed by using for example, beacons to allow wireless communication with the device bodies within the predefined area such as for example, the airport building and in order to allow the person satisfaction with regard to the airport service to be detected by use of the device body. In one example, the person may only be provided with the device body for use once they are in the predefined area and more typically in a secure area and they have to return the device bodies when they leave the secured area.

In another aspect of the invention, the device can be used to provide data relating to a particular item, event or service in which the event is the condition of the person who is using the device such as for example, a health condition so that, if for example, they suffer from a particular condition, such as depression, the person may be encouraged to use the device body user interaction means to record a particular good time or bad time during the person's use of the device body. Furthermore, if the health condition is such that the person is trying to give up consumption of for example, cigarettes, food, alcohol, drugs or the like, then once again, the user device body can be provided to allow the user to provide response data as to their particular activities in relation to that item, event or service in a particular time and the use of the user interaction device at particular times is again recorded and the ongoing healthcare and/or support to the person can be adapted in response to the person's data which is received.

What is claimed is:

1. Apparatus for use by a person to provide feedback relating to at least one parameter in relation to a particular item, event or service which is determined at the start of use of the apparatus in particular period of time and with which the person interacts, said apparatus includes a device body including at least one user interaction means located with or on the device body for selective use by the person, and a transmitter, wherein said data representative of a user interaction is stored in and transmitted from the device body to an intermediate communication device of the person within wireless range or connectable to the device body and subsequently transmitted from the communication device to a database for collection and process means for further processing and said processing means identify the sequence of operation of the interaction means to identify which of a range of possible responses has been input by the person and allocates the response data to the particular item, event or service in relation to which the device body has been associated for said period of time.

2. Apparatus according to claim 1 wherein the apparatus includes control means to allow a type of user interaction to be linked to the at least one particular parameter.

3. Apparatus according to claim 2 wherein the control means is provided as part of the device body.

4. Apparatus according to claim 1 wherein data representing the time of usage of the user interaction means by the person is generated and transmitted from the device body.

5. Apparatus according to claim 1 wherein the device body includes a memory which has a capacity to allow the temporary storage of data from the user interaction means until the data is subsequently transmitted from the device body to said communication device.

6. Apparatus according to claim 5 wherein transmission of the data from the device body to said intermediate communication device is via a wireless transmission.

7. Apparatus according to claim 6 wherein said at least one user interaction means are used by the person to generate data relating to a first parameter and to generate data relating to a second parameter.

8. Apparatus according to claim 7 wherein the user interaction means are selectively operated in different ways to allow data for a particular parameter to be linked thereto.

9. Apparatus according to claim 7 wherein the user interaction means includes a first portion which when selectively used generates data for the first parameter and a second portion which when selectively used generates data for the second parameter.

10. Apparatus according to claim 1 wherein data is transferred from the device body to a remote location for further processing in combination with data received from a number of other person's user interaction means.

11. Apparatus according to claim 1 wherein the device body is provided with retention means to allow the same to be carried on and by the person or is located on an item which the person is to use or is provided at a location at which an event is to occur.

12. Apparatus according to claim 11 wherein the retention means allow the device body to be carried on an item of clothing of the user or to be attachable and carried as part of an article worn by the person and therefore make the device body available for user interaction at the time of use of the item, event or service.

13. Apparatus according to claim 1 wherein the device body includes a power supply to allow the operation of the user interaction means and data transmitter.

14. Apparatus according to any of the preceding claims wherein the apparatus includes a plurality of said device bodies and with control means to allow said plurality of device bodies to be activated at a particular time and deactivated at a particular time so as to define a period of time of available use of said device bodies.

15. Apparatus according to claim 2 wherein the control means allow a number of said device bodies to be selectively rendered operable or inoperable simultaneously.

16. Apparatus according to claim 1 wherein the device body includes visual means to indicate to the person the particular type of their interaction with the user interaction, whether the interaction is valid and/or whether the device body is being reset and a previous interaction has been cancelled.

17. Apparatus according to claim 16 wherein the visual means are provided in the form of one or more LEDs and the colour and/or condition of the LED indicates different states of operation of the device body and the user interaction with the same.

18. Apparatus according to claim 1 wherein the user interaction means is a button which is biased to a first condition and when moved against the biasing force to a second position, data indicating that movement is generated and linked to a particular parameter.

19. Apparatus according to claim 1 wherein the data generated by the user interaction means is transmitted wirelessly to the communication device in the form of a person's mobile phone or other data processing device and then transmitted wirelessly from that device with an ID code to represent the source person, to a further location at which data from a number of person's is collated and processed to provide an indication of at least one parameter linked to the item, event or service.

20. Apparatus according to claim 1 wherein the at least one user interaction button or surface is selectively operable in one or more configurations.

21. Apparatus according to claim 20 wherein the operation of the user interaction button or surface is linked to a particular parameter and/or parameter preference and of which the person is aware so that they can selectively operate the at least one user interaction button or surface.

22. Apparatus according to claim 20 wherein the device or a further device in communication with the device and with which the person can also interact, includes a microphone to accept comments from the user which can be used in combination with the data interaction which they have made via the user interaction means or may be used independently to provide further comments on the particular item, service or event which they are interacting with.

23. A method of generating and collecting data from a person which is representative of their response to an item, event or service, said method comprising the steps of, identifying the item, event or service in relation to which the data is to be generated, providing at least one device body with user interaction means with which a user can interact to indicate usage or a time of experience of the item, event or service and/or an emotion in relation to the said item, event or service, instructing the person to operate the user interaction means to generate data representative of said usage, experience and/or emotion at or close to the same time as the usage or experience occurred and storing and/or transmitting and/or data from the said at least one device body to a remote database and processing means to allow the data to be further processed and characterised in that the said data is first transmitted from the said at least one device body to an intermediate communication device of the person which is within a wireless range or is connectable to the said at least one device body and the at least one device body is used for a period of time in relation to said item, event or service which is determined at the start of the particular period of time of use of the at least one device body.

24. A method according to claim 23 wherein the method includes the step of collecting data from a number of persons and combining the same to provide a report of the usage, experience and/or emotion of a number of persons in relation to the same item, event or service.

* * * * *